United States Patent
Schmitt et al.

(10) Patent No.: US 6,562,168 B1
(45) Date of Patent: *May 13, 2003

(54) METHOD FOR CUTTING AND SEALING AN ABSORBENT MEMBER

(75) Inventors: John Christian Schmitt, Euskirchen-Kirchheim (DE); Torsten Lindner, Kronberg (DE); Italo Corzani, Chieti (IT); Carlisle Mitchell Herron, Remagen (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/720,407

(22) PCT Filed: Jul. 7, 1999

(86) PCT No.: PCT/US99/15287
§ 371 (c)(1),
(2), (4) Date: Dec. 20, 2000

(87) PCT Pub. No.: WO00/01337
PCT Pub. Date: Jan. 13, 2000

(30) Foreign Application Priority Data

Jul. 7, 1998 (EP) ............................................. 98112548

(51) Int. Cl.⁷ ............................................. D06C 25/00
(52) U.S. Cl. ...................... 156/88; 156/251; 156/515; 156/269; 83/22; 427/284; 427/285; 427/289
(58) Field of Search ................................. 156/269, 251, 156/278, 390, 515, 510, 270, 88; 83/14, 22, 169; 427/289, 256, 284, 285, 288; 118/35, 37

(56) References Cited

U.S. PATENT DOCUMENTS

| 4,610,678 A | 9/1986 | Weisman et al. |
| 5,151,092 A | 9/1992 | Buell et al. |
| 6,291,015 B1 * | 9/2001 | Ferguson ..................... 427/284 |
| 6,391,389 B1 * | 5/2002 | Schmitt et al. .............. 427/284 |

FOREIGN PATENT DOCUMENTS

| DE | 19536778 C1 * | 4/1997 | ........... E02D/19/16 |
| EP | 0 846 455 A1 | 6/1998 | |
| WO | WO 93/02861 | 2/1993 | |

* cited by examiner

Primary Examiner—Richard Crispino
Assistant Examiner—Cheryl N. Hawkins
(74) Attorney, Agent, or Firm—Michael P. Hayden; Ken K. Patel

(57) ABSTRACT

A web including a fibrous material and superabsorbent material is fed to a station. The web has a first surface, a second surface, a first side edge and a second side edge. At the station, the operation of applying a superabsorbent material movement obstruction agent and cutting the web into individual absorbent members having a pair of opposing cut ends are carried out simultaneously.

10 Claims, 4 Drawing Sheets

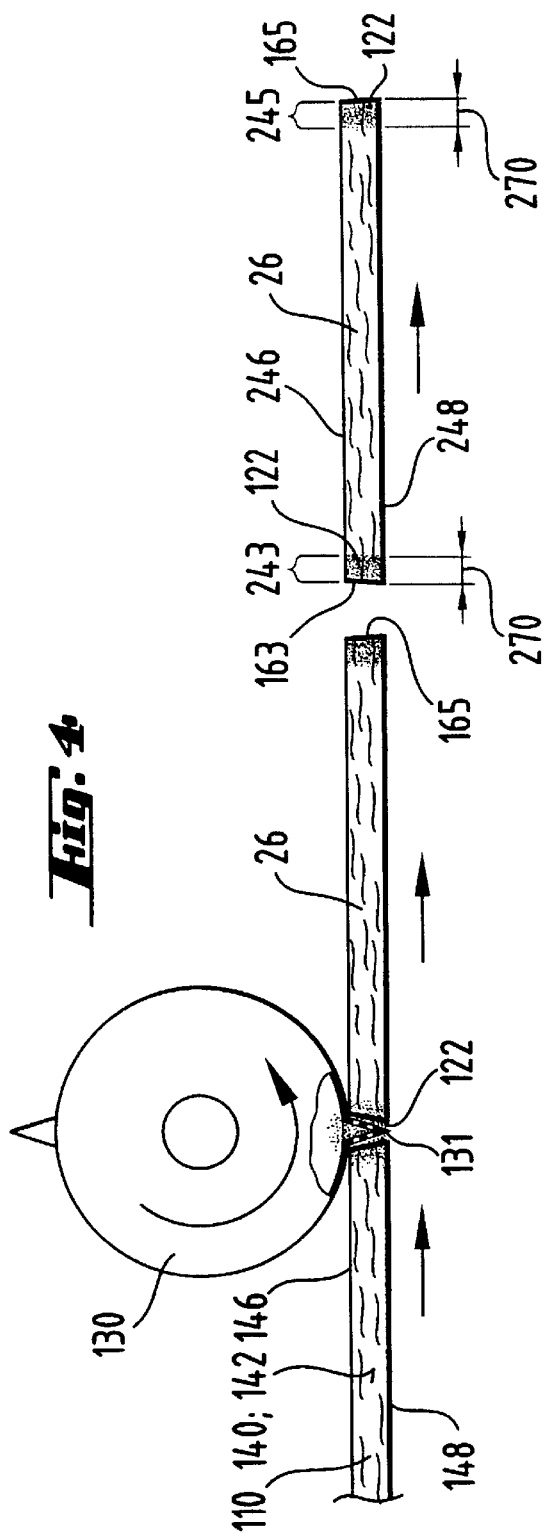
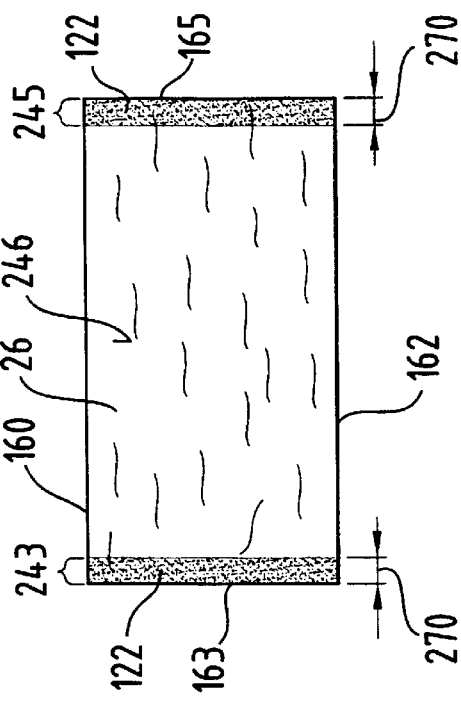

METHOD FOR CUTTING AND SEALING AN ABSORBENT MEMBER

FIELD OF THE INVENTION

This invention relates to a method for cutting and sealing an absorbent member, and more particularly to a method for cutting and sealing an absorbent member which is suitable for use as an absorbent core in a disposable absorbent article.

BACKGROUND OF THE INVENTION

Absorbent webs which comprise masses of fibers, i.e., fibrous web, are well known in the art. Such webs can imbibe liquids, such as discharged body fluids, both by an absorption mechanism wherein fluid is taken up by the fiber material itself and by a wicking mechanism wherein fluid is acquired by, distributed through and stored in the capillary interstices between fibers. One means for improving the absorbency characteristics of such fibrous web structures is to incorporate therein superabsorbent material, such as polymeric gelling material (also referred to as hydrogel-forming material superabsorbent polymers, etc.) which imbibe fluid. The superabsorbent material serves to retain fluid such as discharge body liquids. An absorbent structure of this type wherein hydrogel-forming materials in particulate form are incorporated into fibrous webs is disclosed in Weisman and Goldman, U.S. Pat. No. 4,610,678, issued Sep. 9, 1986.

The improvement in absorbency provided by incorporation of absorbent gelling materials has permitted the realization of absorbent articles, such as disposable diapers, which employ relatively thin absorbent cores and which are, therefore, relatively thin products.

Notwithstanding the existence of absorbent cores as described above, there remains a need to provide absorbent cores which reduce and preferably eliminate the phenomena referred to as gel-on-skin. Gel-on-skin is the situation where absorbent gelling materials escape from the absorbent core and travel through the bodyside liner or topsheet of the absorbent article where they come into contact the wearer's skin.

In prior art continuous lay down operations, fibers and superabsorbent materials are mixed together in a continuous web. The continuous web is then cut into individual absorbent members or cores. The individual absorbent members are then placed between a liquid pervious topsheet and a liquid impervious backsheet to form an absorbent article. Unfortunately, this configuration provided an unsatisfactory product as absorbent gelling material easily penetrated through the topsheet creating unacceptable amounts of gel-on-skin.

One solution to the above continuous lay down operation, was to place another web, such as a tissue or nonwoven web on top of the continuous web and then cut both the tissue and continuous web into individual members comprising the core and the tissue. The individual members were then placed in the product with the tissue positioned between the topsheet and the absorbent core substantially preventing absorbent gelling material from escaping from the uppermost surface of the absorbent core and thus reducing the amount of gel-on-skin.

Unfortunately, when for example, the tissue and the continuous web are cut into individual members, the ends of the absorbent core are left open, i.e., the ends of the absorbent core are not covered by the tissue, allowing absorbent gelling material to escape through the ends of the absorbent core.

It is an object of this invention to provide a method of cutting and sealing an absorbent core via a continuous lay down operation which circumvents the problems of gel-on-skin.

BRIEF SUMMARY OF THE INVENTION

The invention is a method for cutting and sealing an absorbent member. To form the absorbent member, a web comprising a fibrous material and superabsorbent material is fed to a station. The web has a first surface, a second surface, a first side edge and a second side edge. At the station, the operations of applying a superabsorbent material movement obstruction agent and cutting the web into individual absorbent members having a pair of opposing cut ends are carried out simultaneously.

The individual absorbent members have a first surface, a second surface, a first side edge, a second side edge, a first end edge and a second end edge, with the first and second end edges corresponding to the cut ends.

The superabsorbent material movement obstruction agent preferably extends from the first side edge to the second side edge, and from the first surface to the second surface of the individual absorbent members.

The individual absorbent members preferably form an absorbent core in a disposable absorbent article and are positioned between a liquid pervious topsheet and a liquid impervious backsheet.

As used herein the term "superabsorbent material movement obstruction agent" refers an external agent applied to a web comprising fibrous material and superabsorbent material which obstructs the movement of the superabsorbent material through a cut end of the web.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

FIG. 4 is n an enlarged cross-sectional illustration of the simultaneous operation of applying the superabsorbent material movement obstruction agent and cutting the web into individual absorbent members.

FIG. 5 is a plan view of an individual absorbent member.

DETAILED DESCRIPTION OF THE INVENTION

The method of the present invention is particularly suitable for manufacturing absorbent cores for use in disposable absorbent articles. As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner.

Figure 1:
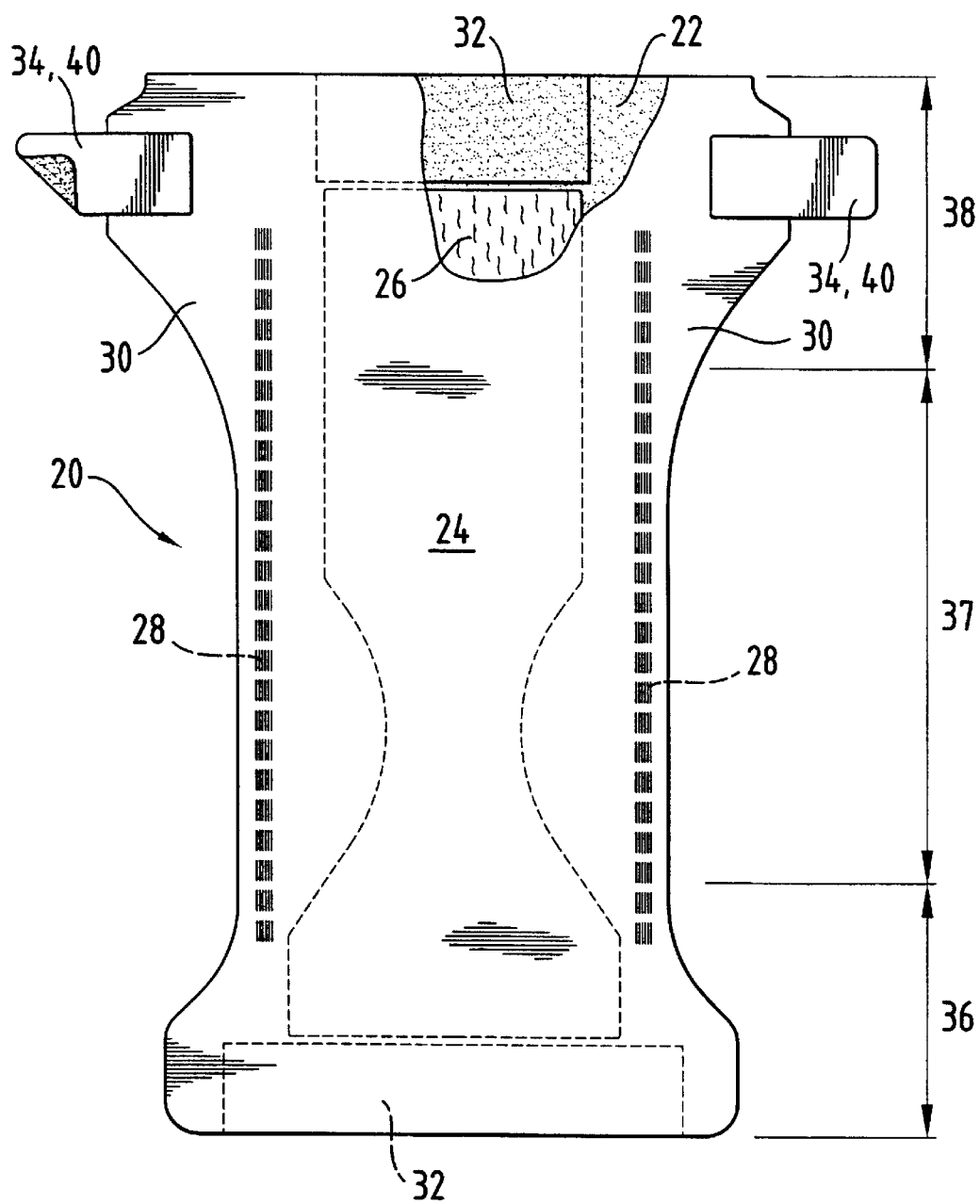
FIG. 1 is a plan view of an absorbent article comprising an absorbent core manufactured in accordance with the method of the present invention.

A preferred embodiment of a unitary absorbent article comprising an absorbent core manufactured by the method of the present invention is the unitary disposable absorbent article, diaper 20, shown in FIG. 1. As used herein, the term "diaper" refers to an absorbent article generally worn by infants and adult incontinent persons and is worn about the lower torso of the wearer. It should be understood, however, that the present invention is also applicable to other absorbent articles such as incontinence briefs, incontinence undergarments, absorbent inserts, diapers holders and liners, feminine hygiene garments, and the like.

With reference to FIG. 1, an absorbent article, such as a diaper 20, generally comprises a liquid pervious topsheet 22, a liquid impervious backsheet 24 joined with the topsheet 22; and an absorbent core 26 intermediate the topsheet 22 and the backsheet 24. The diaper 20 preferably further comprises a front waist region 36, a rear waist region 38, a crotch region 37 positioned between the front waist region 36. and the rear waist region 38, elasticized leg cuffs 28, ear flaps 30, an elastic waist feature 32 and a fastening system 34 comprising at least one tape tab 40. An example of a suitable absorbent article to which the absorbent core of the present invention may be inserted is more fully and completely described in U.S. Pat. No. 5,151,092 issued to Buell et al. on Sep. 29, 1992.

Figure 2:
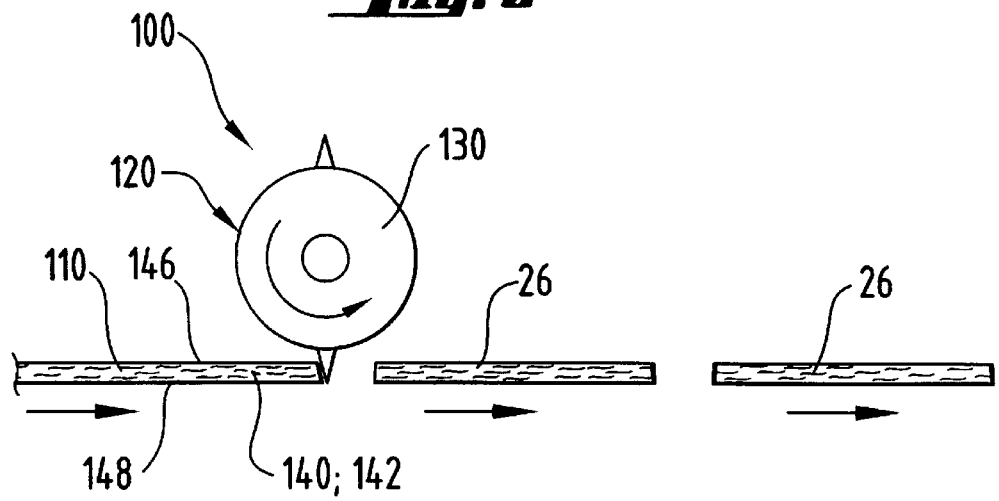
FIG. 2 is a simplified schematic illustration of a continuous lay down method for forming absorbent cores of the present invention.

The absorbent core 26 of the present invention may be produced on the apparatus 100, as shown in FIG. 2. In a preferred embodiment, the apparatus 100 is integrated into a disposable absorbent article manufacturing line such that the absorbent core 26 of the present invention may be manufactured "on-line". (As used herein, the term "integrated" means interconnected process modules that operate concurrently to produce finished products from source materials. The term "on-line" is used to refer to the process of manufacturing the absorbent cores of the present invention on an apparatus that is integrated with the manufacturing line that produces the disposable absorbent articles to which the tape tabs will be joined.)

Examining apparatus 100 in greater detail, a web 110 is provided. Web 110 comprises fibrous material and superabsorbent material. The fibrous material may comprise cellulose fibers, in the form of fluff; modified cellulose fibers such as stiffened cellulose fibers; synthetic fibers such as those made of cellulose acetate, polyvinyl fluoride, polyvinylidene chloride, acrylics, polyvinyl acetate, non-soluble polyvinyl alcohol, polyethylene, polypropylene, polyamides (such as nylon), polyesters, bi-component fibers, tri-component fibers, mixtures thereof and the like. Preferred synthetic fibers have a denier of from about 3 denier per filament to about 25 denier per filament, more preferably from about 5 denier per filament to about 15 denier per filament. Also preferably, the fiber surfaces are hydrophilic or are treated to be hydrophilic.

Suitable superabsorbent materials include but are not limited to discrete particles of absorbent gelling material and superabsorbent fibrous material such as acrylate grafted fibers and superabsorbent modified fibers. The superabsorbent material can be in any form which can be incorporated into a flexible web or sheet to form the web 110. The superabsorbent material, upon contact with fluids such as water or body fluids, absorb such fluids. The superabsorbent material is typically in the form of discrete particles of absorbent gelling material.

Continuous web 110 is fed to station 120 in the direction indicated by the arrows shown in FIG. 2. Web 110 has a first or uppermost surface 146, an opposing second or lowermost surface 148, a first side edge 140 (not shown in FIG. 2), and an opposing second side edge 142. At station 120 the simultaneous operations of applying a superabsorbent material movement obstruction agent 122 to the web 110 and cutting the web into individual absorbent members 26 having a pair of opposing cut ends is carried out. Knife 130 performs the simultaneous operations of applying the superabsorbent material movement obstruction agent 122 to the web 110 and cutting the web into individual absorbent members 26.

Of course other webs may be fed with continuous web 110 to station 120. For example, a tissue or nonwoven web may be positioned adjacent the first surface 146 and/or the second surface 148 and the composite is then fed to station 120. However, for simplicity, only a single web 110 is shown in FIG. 2.

Figure 3:
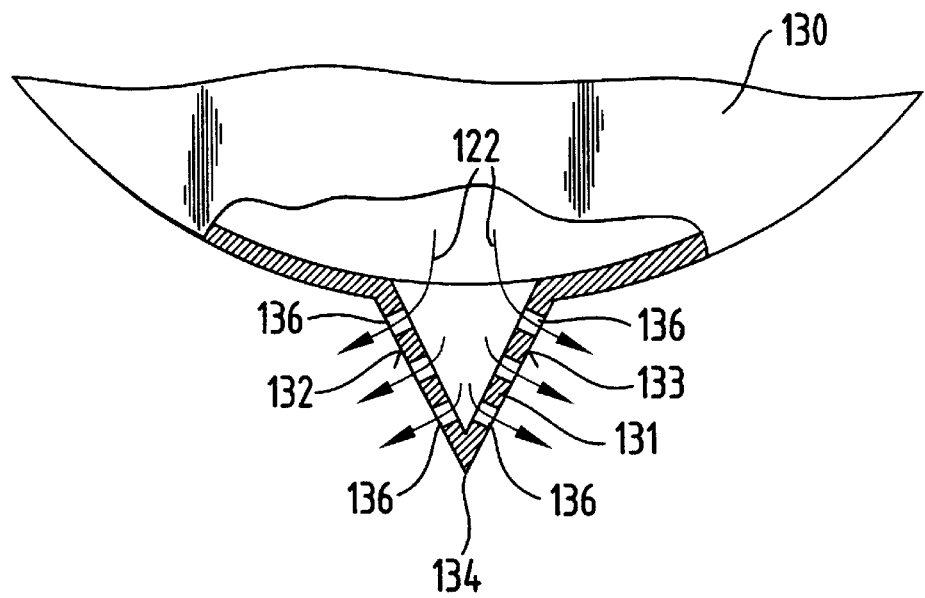
FIG. 3 is an enlarged cross-sectional illustration of a portion of the knife shown in FIG. 2.

FIG. 3 shows an enlarged cross-sectional illustration of a portion of knife 130. Knife 130 has a blade 131 defined by first and second surfaces, 132 and 133, which converge and intersect one another at cutting edge 134. The first and second surfaces 132 and 133 each comprise at least one, and preferably, a plurality of apertures 136 through which superabsorbent material movement obstruction agent 122 may flow. Apertures 136 may be of any shape and size. The number, pattern and spacing of apertures 136 may also be selected as desired.

Referring now to FIG. 4, as blade 131 cuts through web 110, superabsorbent material movement obstruction agent 122 flows through apertures 136 and onto the cut ends of web 110. Referring now to FIGS. 4 and 5, the individual absorbent members 26 have first and second end edges 163 and 165 corresponding to the cut ends of the web 110, a first side edge 160, a second side edge 162, a first or uppermost surface 246, and a second or lowermost surface 248.

Preferably, a sufficient amount of superabsorbent material movement obstruction agent 122 is applied to first and second end edges 163 and 165 to completely seal the ends thus preventing the absorbent gelling material from escaping through the ends of the absorbent members 26. By application of the superabsorbent material movement obstruction agent 122 to only the end edges 163 and 165, each individual absorbent member 26 has a pair of discrete, spaced apart sealing zones 243 and 245. Zone 243 is located adjacent first end edge 163 and zone 245 is located adjacent end edge 165.

Preferably, a thin film of the superabsorbent material movement obstruction agent 122 is applied to the web such that each zone 243 and 245 is relatively thin. However, the superabsorbent material movement obstruction agent 122 may migrate inwardly from the end edges 163 and 165. Preferably, the amount of migration of superabsorbent material movement obstruction agent 122 is minimal such that zones 243 and 245 each have a width dimension 270 of less that about 10 cm, more preferably, less than about 5 cm, and most preferably less than about 1 cm.

As can be seen in FIG. 4 the superabsorbent material movement obstruction agent extends along the end edges 163 and 165 through the entire absorbent member 26 from the first surface 246 to the second surface 248.

Zones 243 and 245 preferably occupy less than 30% of the volume of absorbent member 26, more preferably less than 20% of the volume of absorbent member 26, and most preferably less than 10% of the volume of absorbent member 26.

Suitable agents for the superabsorbent material movement obstruction agent include, but are not limited, to polymeric solutions or emulsions, both natural (e.g. natural rubber latex) and synthetic, in which the liquid is water or any other suitable liquid or mixture of liquids. Waterborne emulsions are preferred and more preferred are waterborne emulsions of acrylic or vinylic adhesive polymers.

Other suitable agents for the superabsorbent material movement obstruction agent also include thermoplastic polymers or polymeric compositions having a softening point, as determined by the ASTM Method E 28 "Ring and Ball", in the range between 50° C. and 300° C. Preferably such thermoplastic polymer or polymeric composition is a wax or a composition containing at least 50% by weight of a wax, such wax or composition preferably having a softening point less than about 180° C. More preferably such thermoplastic agent (being it a polymer, a wax or a composition derived therefrom) is or contains at least 50% by weight of a copolymer having, at least as one of its co-monomers, Acrylic Acid, Acrylamide, Acrylic Esters and/or derivatives therefrom.

The superabsorbent material movement obstruction agent is preferably not applied to the entire web, but only in discrete, spaced apart zones. While the superabsorbent material movement obstruction agent does provide the benefit of obstructing the movement of the superabsorbent material through the cut end of a web, it may have some negative effects if applied to the entire web. For example, the agent may increase the stiffness of the web such that it becomes uncomfortable for the wearer if applied to the entire web. The agent may inhibit some of the absorbent properties of the web and thus would negatively impact the absorbent article which employed a web having the agent applied to the entire web. Thus, in order to achieve the desired effect of obstructing the movement of the superabsorbent material through the cut end of a web without negatively impacting the performance, comfort or other properties and characteristics of the web and an absorbent article which employs such a web, the superabsorbent material movement obstruction agent is applied to the web in only discrete, spaced apart zones.

Figure 6:
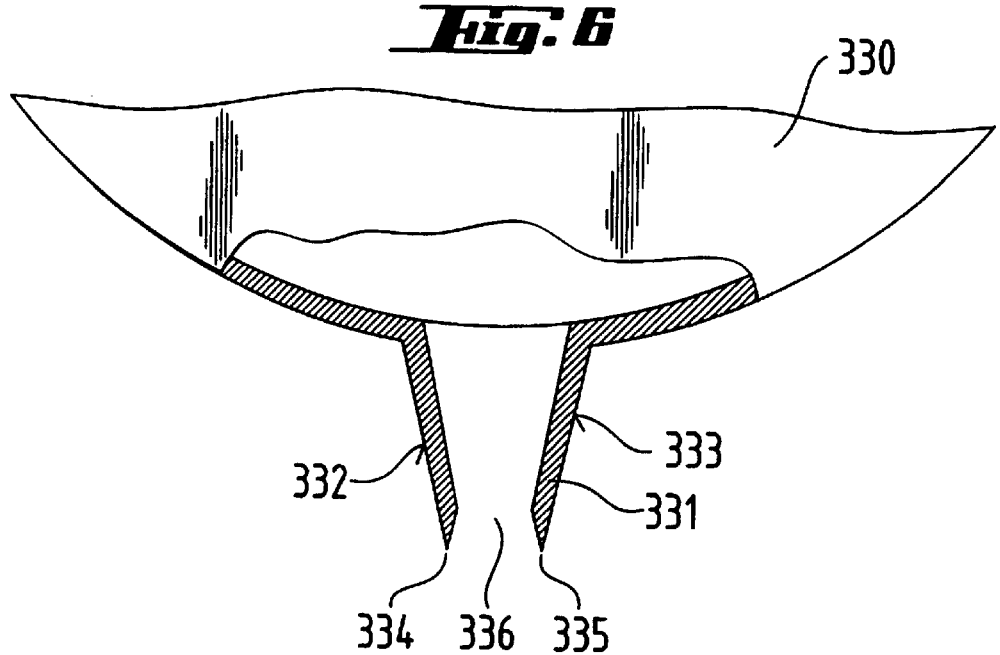
FIG. 6 is an enlarged cross-sectional illustration of another knife embodiment of the present invention.

Referring now to FIG. 6 there is shown an enlarged cross-sectional illustration of another knife embodiment of the present invention. Knife 330 has a blade 331 defined by first and second surfaces, 332 and 333. Unlike knife 130 illustrated in FIG. 3, first and second surfaces 332 and 333 of knife 330 do not intersect one another at single cutting edge. Instead, first and second surfaces 332 and 333 converge to a pair of cutting edges 334 and 335. Between the cutting edges 334 and 335 is a slot 336 through which superabsorbent material movement obstruction agent may flow.

Figure 7:
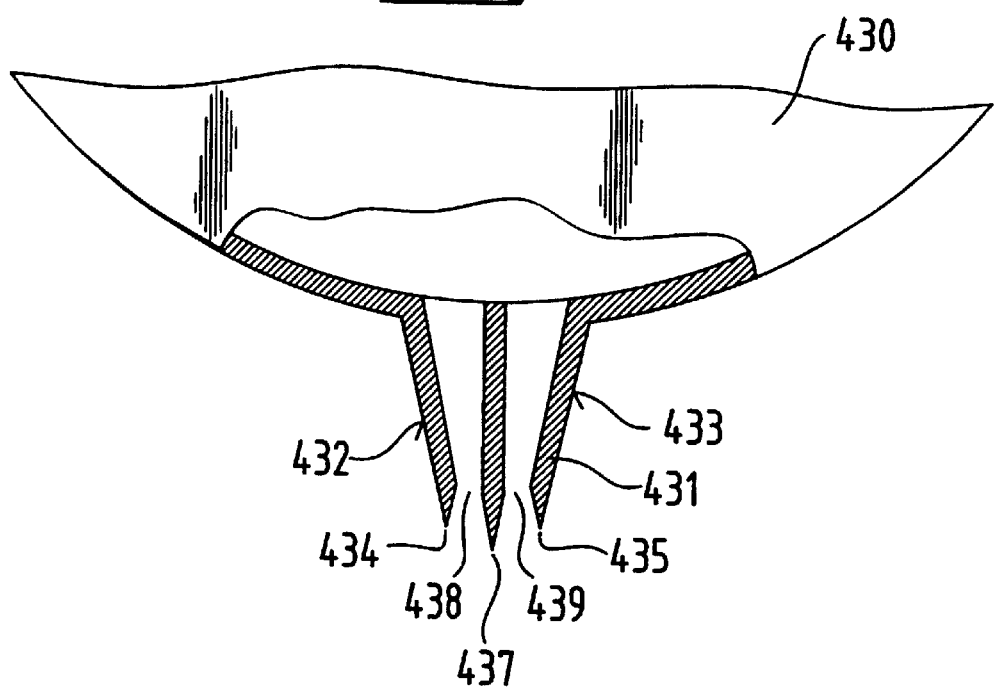
FIG. 7 is an enlarged cross-sectional illustration of another knife embodiment of the present invention.

Referring now to FIG. 7 there is shown an enlarged cross-sectional illustration of another knife embodiment of the present invention. Knife 430 has a blade 431 defined by first and second surfaces, 432 and 433. Similar to knife 330 shown in FIG. 6, first and second surfaces 432 and 433, do not intersect one another at single cutting edge. Instead, they converge to a pair of cutting edges 434 and 435. In addition, a third cutting edge 437 is positioned between cutting edges 434 and 435. Third cutting edge 437 may extend outward from knife 430 the same distance as edges 434 and 435, more than edges 434 and 435, or less than edges 434 and 435. Preferably, the third cutting edge 437 extends outwardly from knife 430 more than edges 434 and 435. Between the cutting edges 434 and 437 is a first slot 438 and between cutting edges 435 and 437 is a second slot 439. Superabsorbent material movement obstruction agent may flow through each of slots 438 and 439.

In another embodiment of the method of the present invention, the superabsorbent material movement obstruction agent is transferred to the knife from an external device such as a rubber roll, a slot coater, a spray gun, or any other suitable means known in the art. Subsequently, the superabsorbent material movement obstruction agent is transferred to the web.

When incorporated into an absorbent article, such as diaper 20 shown in FIG. 1, zones 243 and 245 of absorbent member 26 are preferably positioned within the front waist region 36 and the rear waist region 38, respectively. While, zones 243 and 245 may be of such dimension that they extend into crotch region 37, this is not preferred.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for cutting and sealing an absorbent member (26), said method comprising the steps of:
    a) feeding a web (110) comprising a fibrous material and a superabsorbent material, said web having a first side edge (140) and a second side edge (142); and
    b) using a mechanical knife to simultaneously apply a superabsorbent material movement obstruction agent (122) to said web and cut said web into individual absorbent members (26) having a pair of opposing cut ends.

2. The method of claim 1 wherein said individual members (26) have a first surface (246), a second surface (248), a first side edge (160), a second side edge (162), a first end edge (163) and a second end edge (165), said first and second end edges corresponding to said cut ends, and discrete, spaced apart sealing zones (243, 245) formed by the superabsorbent material movement obstruction agent.

3. The method of claim 2 wherein each zone extends from said first side edge to said second side edge and from said first surface to said second surface.

4. The method of claim 3 wherein said zones of superabsorbent material movement obstruction agent have a width of less than about 10 cm.

5. The method of claim 3 wherein said sealing zones of superabsorbent material movement obstruction agent have a width of less than about 5 cm.

6. The method of claim 3 wherein said sealing zones of superabsorbent material movement obstruction agent have a width of less than about 1 cm.

7. The method of claim 1 wherein said superabsorbent material movement obstruction agent is a material selected from the group of polymeric solutions or polymeric emulsions.

8. The method of claim 1 wherein said superabsorbent material movement obstruction agent is a thermoplastic polymer or thermoplastic polymeric composition having a softening point in the range between 50° Celsius and 300° Celsius.

9. The method of claim 8 wherein said thermoplastic polymer or thermoplastic polymeric composition is a wax or a composition containing at least 50% by weight of a wax.

10. The method of claim 7 wherein said polymeric solutions or polymeric emulsions are either natural or synthetic.

* * * * *